United States Patent [19]

Babad et al.

[11] Patent Number: 5,011,993
[45] Date of Patent: Apr. 30, 1991

[54] METHOD FOR THE PREPARATION OF α[[(1,1-DIMETHYLETHYL)AMINO]ME-THYL]-4-HYDROXY-1,3-BENZENEDIME-THANOL

[75] Inventors: Esther Babad, West Orange; Nicholas Carruthers, Springfield; Martin Steinman, Livingston, all of N.J.

[73] Assignee: Schering Corporation, Kenilworth, N.J.

[21] Appl. No.: 512,232

[22] Filed: Apr. 20, 1990

Related U.S. Application Data

[62] Division of Ser. No. 431,264, Nov. 3, 1989, Pat. No. 4,952,729, which is a division of Ser. No. 903,813, Sep. 5, 1986, abandoned.

[51] Int. Cl.$^5$ .................. C07C 249/02; C07C 251/24
[52] U.S. Cl. .................................................. 564/273
[58] Field of Search ........................................ 564/273

[56]        References Cited
        U.S. PATENT DOCUMENTS 3,644,353  2/1972  Lunts et al. ..................... 564/363
4,021,485  5/1977  Schromm et al. ................. 564/358
4,112,583  3/1977  Wetterlin et al. ................ 564/358
4,154,761  5/1979  Collins et al. .................... 564/365

FOREIGN PATENT DOCUMENTS 2340189  2/1975  Fed. Rep. of Germany .
1200886  8/1970  United Kingdom .
1247370  9/1971  United Kingdom .

OTHER PUBLICATIONS

Collin, Journal of Medicinal Chemistry, 13, No. 4, 674 (1970).

Primary Examiner—Richard L. Raymond
Attorney, Agent, or Firm—Gerald S. Rosen; John J. Maitner

[57]             ABSTRACT

There is disclosed an improved process for preparing albuterol which comprises reacting a 5-(haloacetyl)-2-hydroxybenzaldehyde with 1,1-dimethylethanamine in an organic solvent and in an inert atmosphere to form 5-[[(1,1-dimethylethyl)amino]acetyl]- 2-hydroxybenzaldehyde and reducing the carbonyl functions to the corresponding hydroxy groups to form albuterol.

6 Claims, No Drawings

METHOD FOR THE PREPARATION OF α¹[[(1,1-DIMETHYLETHYL)AMINO]METHYL]-4-HYDROXY-1,3-BENZENEDIMETHANOL

This is a division of application Ser. No. 431,264, filed 11-3-89, now U.S. Pat. No. 4,952,729, which is a division of application Ser. No. 903,813, filed Sept. 5, 1986, now abandoned.

BACKGROUND $\alpha^1$-[[(1,1-Dimethylethyl)amino]methyl]-4-hydroxy-1,3-benzenedimethanol, a substance known as albuterol and salbutamol, is a potent long-lasting $\beta$-adrenoceptor stimulant that is orally effective and shows highly selective action on bronchial smooth muscle. Albuterol is indicated for the relief of bronchospasm in patients with reversible airway disease.

Albuterol has been prepared, see Irish Patent Specification No. 31391, Aug. 9, 1972, starting from the appropriate acetophenone derivative methyl-5-(bromoacetyl-2-hydroxybenzoate, by condensation with N-(1,1-dimethylethyl)benzenemethanamine in the presence of base to form the ketonic ester, methyl-5[[(1,1-dimethylethyl)(phenylmethyl)-amino]acetyl]-2-hydroxybenzoate. The ketonic ester is reduced with lithium aluminum hydride in tetrahydrofuran under nitrogen to yield $\alpha^1$-[[(1,1-dimethylethyl)-(phenylmethyl)amino]methyl]-4-hydroxy-1,3-benzenedimethanol which is subsequently debenzylated with hydrogen in the presence of palladium on carbon catalyst to produce albuterol.

We have found that albuterol can be conveniently prepared in good yield by reacting 5-(halo acetyl)-2-hydroxybenzaldehyde with 1,1-dimethylethanamine followed by reduction of the intermediate ketone compound, 5-[[(1,1-dimethylethyl)amino]acetyl]-2-hydroxybenzaldehyde. The synthesis does not require protection of any of the reactive functional groups on either of the reactants, for example the hydroxy or aldehyde function of the 2-hydroxybenzaldehyde starting material or the amino function of the 1,1-dimethylethanamine.

SUMMARY OF THE INVENTION

The present invention provides a method for the preparation of albuterol in good yield without the need to protect any of the functional groups on any of the reagents.

The process of this invention is a novel multi-step process in which certain individual steps are novel and in which certain of the intermediates are novel.

DETAILED DESCRIPTION OF THE INVENTION

In a preferred embodiment described below, albuterol is produced by following the reaction sequence shown below:

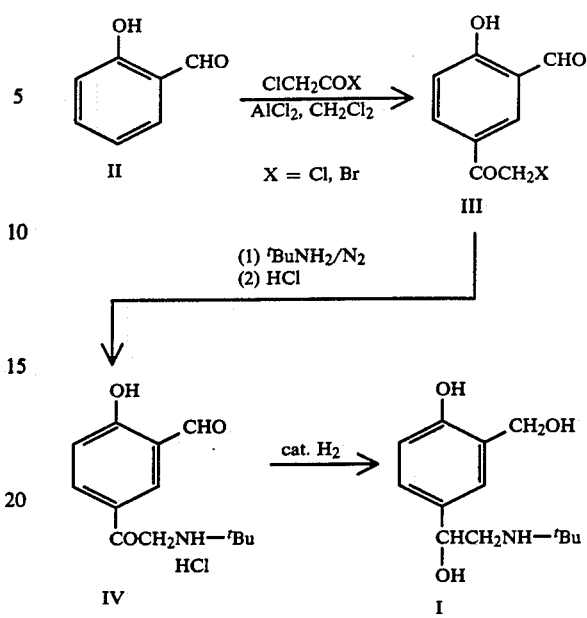

Step A 5-(Haloacetyl)-2-hydroxybenzaldehyde (III) is prepared by reacting 2-hydroxybenzaldehyde (II) with a haloacetylhalide under Friedel-Crafts conditions. Such Friedel-Crafts procedures are known to those skilled in the art and are described in the chemical literature, for example, "Friedel-Crafts and Related Reactions", George A. Olah (Ed.), Interscience Publisher (4 Volumes). Haloacetylhalide compounds that can be utilized as the starting material include bromoacetylchloride, chloroacetylchloride, and the like. The title compound may also be prepared in a two step procedure, by means of acetylation then halogenation. In carrying out the instant process any Lewis acid can be employed as the catalyst; aluminum trichloride is the preferred catalyst. Usually the reaction will be carried out in an organic solvent inert towards the reactants, for example, dichloromethane, 1,2-dichloroethane, nitrobenzene, chlorobenzene. The preferred solvents include dichloromethane and nitrobenzene. The reaction is carried out at elevated temperature, preferably at a temperature of from 40° to 100° C. Isolation of the resulting 5-(haloacetyl)-2-hydroxybenzaldehyde (III) can be carried out employing conventional procedures well known in the art, such as column chromatography, recrystallization, and the like. Any ortho isomer formed during the reaction is removed by recrystalization.

Step B

5-[[(1,1-Dimethylethyl)-amino]acetyl-2-hydroxybenzaldehyde (IV) is prepared by reacting 5-(haloacetyl)-2-hydroxybenzaldehyde (III) with 1,1-dimethanethylamine. In carrying out this reaction, the 1,1-dimethylethanamine is present in excess, for example, 10 to 1 and preferably 3 to 1 of 1,1-dimethylethanamine to (III).

The reaction of 1,1-dimethylethanamine with the halo derivative (III) initially produces the Schiff base having the structural formula V which may be isolated but it is not necessary to do so.

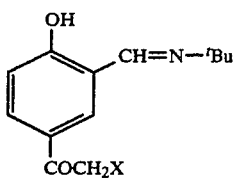

V

Further reaction of V with 1,1-dimethylethanamine produces the compound of structural formula VI

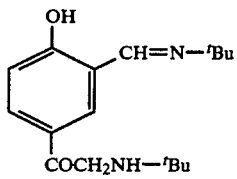

VI

Treatment of the Schiff base VI with aqueous acid leads to hydrolysis of said compound and precipitation of IV as the acid addition salt.

In order to obtain the desired compound IV in good yield it is essential that the reaction be carried out under an inert atmosphere, for example under argon, nitrogen and the like. The reaction is carried out by suspending the haloacetyl compound III in an organic solvent and treating the suspension with 1,1-dimethylethanamine at a temperature from room temperature to reflux of the mixture. Examples of organic solvents that can be utilized in this reaction include 2-propanol, 1,1-dimethylethanol, 2-methyl-1-propanol, 2-butanol, and the like. The preferred solvent is 2-propanol.

The amino compound IV is conveniently isolated as the acid addition salt. Acids that can be employed to form these salts are any suitable inorganic or organic acid, for example, include hydrochloric, sulfuric, 4-methylbenzenesulfonic.

If the reaction of the haloacetyl compound (III) with 1,1-dimethylethanamine is not carried out in an inert atmosphere it was discovered that the compound of structural formula VI in the presence of oxygen undergoes the following reaction:

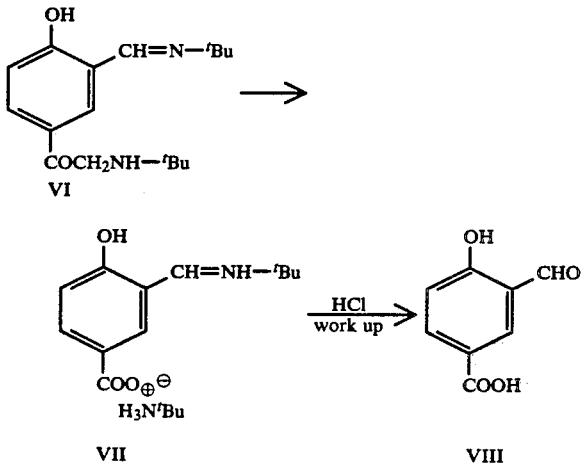

This undesirable side reaction can be prevented by running the reaction under an inert atmosphere.

Step C

The keto and aldehyde groups of the acid addition salt from Step B are then reduced to alcoholic groups by conventional methods well known to persons skilled in the art. In the preferred method the keto and aldehyde groups are reduced by catalytic hydrogenation. Suitable catalysts include palladium on carbon, or other platinum metals, and the like. Such methods are known to those skilled in the art and are described in "Catalytic Hydrogenation Over Platinum Metals", Paul N. Rylander, Academic Press, 1967, and "Catalytic Hydrogenation In Organic Synthesis", Paul N. Rylander, Academic Press, 1979. The hydrogenation can be carried out by dissolving the acid addition salt of compound (IV) in an appropriate solvent, such as anhydrous methanol, ethanol, 2-propanol, and the like. After addition of base, such as sodium methoxide, the hydrogenation is carried out in a suitable apparatus, for example a Parr apparatus. The resulting product is isolated by conventional techniques.

Alternatively, the keto and aldehyde groups can be reduced to the alcohol with suitable hydrides, for example sodium borohydride, lithium borohydride or amine boranes, for example, 1,1-dimethylethylaminoborane, in an organic solvent. Methods are described in "Reductions in Organic Chemistry", Milos Hudlicky, Ellis Horwood, 1984.

$\alpha^1$[[(1,1-Dimethylethyl)amino]methyl]-4-hydroxy-1,3-benzenedimethanol is conveniently isolated as the free base or as the acid addition salt. Acids that can be employed to form the acid addition salt are suitable inorganic and organic acids such as hydrochloric, sulfuric, 4-methylbenzenesulfonic acid, and the like.

EXAMPLE I

Step A

1.

5-(BROMOACETYL-)-2-HYDROXYBENZALDE-HYDE

Preparation (a)

Aluminum trichloride (333 g) is suspended in dichloromethane (350 ml) with stirring and heated to reflux temperature. To this slurry is added bromoacetyl chloride (99 g) in dichloromethane (75 ml) and after 30 minutes 2-hydroxybenzaldehyde (61.1 g) in dichloromethane (75 ml) is added dropwise. The reaction mixture is refluxed for 16 hours and then cautiously poured onto ice (3 kg), deionized water (300 ml) and dichloromethane (500 ml) with stirring. Once the addition is complete the mixture is stirred for a further 15 minutes and the pH of the aqueous phase adjusted to pH 1-2 (pH paper) with concentrated hydrochloric acid if necessary. The organic layer is separated and the aqueous extracted with dichloromethane (3×250 ml). The organic portions are combined, washed with deionized water (2×250 ml) and saturated sodium chloride solution (500 ml). The dichloromethane solution is dried over anhydrous magnesium sulfate and the dried solution evaporated under reduced pressure to give an oily solid (107 g). The solid is slurried with a mixture of dichloromethane (20 ml) and diethylether (180 ml) and filtered. The solid obtained is dried in vacuo at 50° to give 83 g of a mixture (6:1) of the title compound and 5-(chloroacetyl)-2-hydroxybenzaldehyde.

NMR (CDCl$_3$): δ 4.35 (s, CH$_2$—Br);

4.65 2H (s, CH$_2$—Cl);
7.05 (1H, d, J=10 Hz);
8.00–8.30 (2H, m);
9.90 (1H, s);
11.50 (1H, s).

Preparation (b)

Aluminum tribromide (26.7 g) in dibromomethane (100 ml) is treated with bromoacetylbromide (5.1 g) with stirring. After 30 minutes this solution is treated with 2-hydroxybenzaldehyde (2.4 g). The reaction mixture is then heated at 80°–90° (external oil bath) for 18 hours and cautiously poured onto ice (800 g) with stirring. The organic layer is separated and the aqueous extracted with dichloromethane (2×100 ml). The organic portions are combined, washed with saturated sodium chloride solution (2×250 ml) and dried over anhydrous magnesium sulfate. The dried solution is evaporated under reduced pressure to afford a brown oil. Purification is achieved by chromatography on silica gel eluting with hexane: ethylacetate mixtures to give 0.46 g of the title compound as a light crystalline solid.

NMR (CDCl$_3$): δ 4.4 (2H, s);
7.05 (1H, d, J=10 Hz);
8.00–8.03 (2H, m);
9.90 (1H, s);
11.40 (1H, s).
IR (KBr): ν 1650 cm$^{-1}$;
UV (CH$_3$CN): λmax. 243 nm (ε=24,082);
Found: C, 44.47; H, 2.83 and Br, 32.24%.

2. 5-(CHLOROACETYL)-2-HYDROXYBENZALDEHYDE

Preparation (a)

Aluminum trichloride (100 g) is suspended in dichloromethane (125 ml) with stirring and heated to reflux temperature. This slurry is treated with chloroacetylchloride (28.2 g) and after 30 minutes with 2-hydroxybenzaldehyde (24.4 g) dropwise. Once addition is complete the reaction mixture is heated at reflux for a further 18 hours and poured cautiously onto ice (1 kg), deionized water (100 ml) and dichloromethane (100 ml). The solution is stirred for 15 minutes and the pH of the aqueous layer adjusted to pH 1–2 (pH paper) by addition of concentrated hydrochloric acid if necessary. The organic layer is separated and the aqueous extracted with dichloromethane (3×150 ml). The organic portions are combined, washed with deionized water (2×250 ml), saturated sodium chloride solution (500 ml) and dried over anhydrous magnesium sulfate. The dried solution is evaporated under reduced pressure to give an oily solid. The solid is dissolved in hot 2-butanone (70 ml) from which the title compound crystallizes upon cooling. The title compound (16 g) is isolated by suction filtration.

NMR (CDCl$_3$): δ 4.65 (2H,s); 7.06 (1H, d, J=10 Hz); 8.00–8.26 (2H, m); 9.95 (1H, s); 11.45 (1H, s).
IR (KBr): ν 1650 cm$^{-1}$;
UV (CH$_3$CN): λmax. 241 nm (ε=27,952);
Found: C, 54.41; H, 3.45 and Cl, 17.72%.

Preparation (b)

Aluminum trichloride (180 g) is suspended in dichloromethane (500 ml) and heated with stirring to reflux temperature. To this slurry is added phosphoryl chloride (12.5 ml) in dichloromethane (12.5 ml), chloroacetylchloride (40.5 ml) in dichloromethane (40 ml) and after 60 minutes 2-hydroxybenzaldehyde (18.8 ml) in dichloromethane (20 ml). The reaction mixture is refluxed for 24 hours and then cautiously added to ice (1.5 kg), deionized water (500 ml) and dichloromethane (500 ml) with stirring. Once addition is complete the mixture is agitated for 30 minutes and the pH of the aqueous phase adjusted to pH 1–2 (pH paper) by addition of concentrated hydrochloric acid, if necessary. The organic layer is separated and the aqueous extracted with dichloromethane (2×200 ml). The organic portions are combined, washed with deionized water (2×200 ml) and concentrated in vacuo (to approximately 150 ml). The concentrated solution is diluted with methylbenzene (300 ml) and evaporated in vacuo (to approximately 100 ml) whereupon 10.4 g of the title compound is isolated by suction filtration. Further purification is achieved by recrystallization from 2-butanone.

Step B

1. 5-[[(1,1-DIMETHYLETHYL)AMINO]ACETYL]-2-HYDROXYBENZALDEHYDE HYDROCHLORIDE

Preparation (a)

5-(Bromoacetyl)-2-hydroxybenzaldehyde (10.8 g) is suspended in 2-propanol (40 ml) with stirring under an inert atmosphere and treated with 1,1-dimethylethanamine (14 ml). This solution is heated at reflux temperature for 2 hours and treated with a mixture of 12M hydrochloric acid (11.1 ml) and 2-propanol (9 ml). After stirring for a further 18 hours and cooling to room temperature a solid is isolated by filtration and dried in vacuo at 50°. The dried material is slurried with 2-propanol (100 ml), stirred for 18 hours, filtered and dried in vacuo at 50°. In this manner 7 g of the title compound is obtained as a free flowing powder.

NMR ((CD$_3$)$_2$SO): δ 1.4 (9H,s); 4.65 (2H, s); 7.3 (1H, d, J=10 Hz); 8.1–8.4 (2H, m); 10.3 (1H, s).
IR (KBr): ν 1670 cm$^{-1}$;
UV (CH$_3$CN): 243 nm (ε=22,411);
Found: C, 57.43; H, 6.63, and N, 4.88.

Preparation (b)

5-(Chloroacetyl)-2-hydroxybenzaldehyde (10 g) is suspended in 2-propanol (60 ml) with stirring at room temperature under an inert atmosphere. This slurry is treated with 1,1-dimethylethanamine (16.4 ml) and heated at reflux for 1 hour then treated with a mixture of 12M hydrochloric acid (13.0 ml) and 2-propanol (20 ml). The reaction mixture is allowed to cool to room temperature and stir for a further 18 hours. Filtration of the reaction mixture affords the title compound (6.2 g) after washing with diethylether (50 ml) and drying in vacuo at 50°.

Preparation (c)

5-(Bromoacetyl)-2-hydroxybenzaldehyde (109 g) is suspended in 2-propanol (920 ml) and cooled to −3° C. with stirring. The reaction mixture is treated with 1,1-dimethylethanamine (29.24 g) and stirred at −3° to 0° C. for 30 minutes whereupon precipitation occurs. The reaction mixture is allowed to warm to room temperature, stirred for 90 minutes then cooled to 10° C. and filtered. The solid obtained is washed with ice cold 2-propanol (2×100 ml) and dried in vacuo at 55° C. for 18 hours providing 89 g of 2-bromo-1-[3-[[(1,1-dimethylethyl)imino]methyl]-4-hydroxyphenyl]ethanone.

NMR ((CDCl$_3$: (CD$_3$)$_2$SO): δ 1.43 (9H,s); 4.45 (2H, s); 6.80 (1H, d, J=10 Hz); 7.75–8.10 (2H, m); 8.45 (1H, brs).

IR (KBr): ν 1625 cm$^{-1}$;
UV (CH$_3$CN): λmax. 250 nm (ε=18,854);
Found: C, 52.68; H, 5.35; N, 4.77; and Br, 26.77%.

2-Bromo-1-[3-[[(1,1-dimethylethyl)imino]methyl]-4-hydroxyphenyl]ethanone (11.93 g) is suspended in 2-propanol (100 ml) under an inert atmosphere and treated with 1,1-dimethylethanamine (8.8 g) and a further portion of 2-propanol (50 ml). The solution is heated at 80° until all the starting material is consumed. The reaction mixture is cooled to −10°, treated with 12M hydrochloric acid (11 ml) and 2-propanol (50 ml). Stirring is continued for an additional 18 hours during which time the solution warms to room temperature. A solid is isolated from the solution, slurried in 2-propanol (50 ml), filtered and dried in vacuo at 50° giving 5.0 g of 5-[[(1,1-dimethylethyl)amino]acetyl]-2-hydroxybenzaldehyde hydrochloride.

Preparation (d)

2-(Chloroacetyl)-2-hydroxybenzaldehyde (1 g) is suspended in 2-propanol (10 ml) with stirring at room temperature. The slurry is treated with 1,1-dimethylethanamine (0.63 ml) and stirred for 18 hours. Filtration of the reaction mixture affords 0.4 g 2-chloro-1-[3-[[(1,1-dimethylethyl)imino]methyl-4-hydroxyphenyl]ethanone as a yellow solid.

NMR ((CDCl$_3$): δ 1.4 (9H,s); 4.55 (2H, s); 6.85 (1H, d, J=10 Hz); 7.70–7.90 (2H, m); 8.23 (1H, brs).

IR (KBr): ν 1600 cm$^{-1}$;
UV (CH$_3$CN): λmax. 249 nm (ε=23,563);
Found: C, 61.50; H, 6.48; N, 5.26; and Cl, 13.90%.

2-Chloro-1-[3-[[(1,1-dimethylethyl)imino]methyl]-4-hydroxyphenyl]ethanone (10 g) is suspended in 2-propanol (60 ml) with stirring at room temperature under an inert atmosphere. This slurry is treated with 1,1-dimethylethanamine (16.4 ml) and heated at reflux for 1 hour then treated with a mixture of 12M hydrochloric acid (13.0 ml) and 2-propanol (20 ml). The reaction mixture is allowed to cool to room temperature and stir for an additional 18 hours. Filtration of the reaction mixture affords (6.2 g) of 5-[[(1,1-dimethylethyl)amino]acetyl]-2-hydroxybenzaldehyde hydrochloride after washing with diethylether (50 ml) and drying in vacuo at 50°.

2.
5-[[(1,1-DIMETHYLETHYL)AMINO]ACETYL]-2-HYDROXYBENZALDEHYDE 4-METHYLBENZENESULFONATE

Preparation (a)

5-(Bromoacetyl)-2-hydroxybenzaldehyde (18.0 g) is suspended in 2-propanol (100 ml) at 0°, under an inert atmosphere, treated with 1,1-dimethylethanamine (23.4 ml) and allowed to warm to room temperature. Stirring is continued for a further 50 minutes and the solution is treated with a mixture of 4-methylbenzenesulfonic acid monohydrate (42.3 g), 2-propanol (35 ml) and deionized water (20 ml). This solution is stirred for a further 18 hours, filtered, the residue washed with diethylether (50 ml), then dried in vacuo at 50°. In this manner the title compound (20.0 g) is obtained as a free flowing powder.

NMR ((CD$_3$)$_2$SO): δ 1.37 (9H,s); 2.30 (3H,s); 3.37 (2H,s); 7.12, 7.50 (4H, A$_2$B$_2$, J=9 Hz); 7.20 (1H, d, J=10 Hz); 8.25 (1H, dd, J=2, 10 Hz); 8.40 (1H, d, J=2 Hz).

Preparation (b)

5-(Chloroacetyl)-2-hydroxybenzaldehyde (7.9 g) is suspended in 2-propanol (50 ml) under an inert atmosphere and treated, with stirring, with 1,1-dimethylethanamine (13 ml). The mixture is heated at reflux for 2 hours and treated with a mixture of 4-methylbenzenesulfonic acid monohydrate (23.5 g), 2-propanol (16 ml) and deionized water (8 ml). The solution is stirred for a further 18 hours, filtered, the residue washed with diethylether (50 ml) and dried in vacuo at 50°. The solid isolated is washed with 2-propanol (100 ml) and dried in vacuo at 50° giving the title compound (9.02 g).

3.
5-[[(1,1-DIMETHYLETHYL)AMINO]-ACETYL]-2-HYDROXYBENZALDEHYDE HEMISULFATE 5-(Bromoacetyl)-2-hydroxybenzaldehyde (10 g) is suspended in 2-propanol (60 ml) under an inert atmosphere and cooled to 0°. To the stirring slurry is added 1,1-dimethylethanamine (13 ml) and the reaction mixture permitted to warm to room temperature and stir for 50 minutes. The solution is then treated with a mixture of concentrated sulfuric acid (3.5 ml), 2-propanol (6.5 ml) and deionized water (5 ml). The reaction mixture is stirred for a further 18 hours whereupon the title compound (10.2 g) is isolated by filtration and dried in vacuo at 50°.

NMR ((CD$_3$)$_2$SO): δ 1.41 (9H,s); 4.68 (2H,s); 7.15 (1H, d, J=10 Hz); 8.1–8.45 (2H, m); 10.35 (1H, s).

1. Step C

α$^1$-[[(1,1-DIMETHYLETHYL)AMINO]METHYL]-4-HYDROXY-1,3-BENZENEDIMETHANOL

Preparation (a)

5-[[(1,1-Dimethylethyl)amino]acetyl]-2-hydroxybenzaldehyde hydrochloride (0.774 g) is dissolved in anhydrous methanol (20 ml) at ice-bath temperature. To the solution is added sodium methoxide (0.154 g), with stirring, and after 5 minutes 5% palladium on carbon (0.23 g). The mixture is hydrogenated at room temperature, at 60 psi of hydrogen in a Parr apparatus. After 10 hours the reaction mixture is filtered through a pad of Celite ® and the filtrate evaporated to give the title compound (0.6 g).

In a similar manner the reaction mixture may be filtered before addition of catalyst and again after hydrogenation is complete.

NMR (CD$_3$OD): δ 1.3 (9H,s); 2.9 (2H, m); 4.65–4.90 (3H, m); 6.80 (1H, d, J=9 Hz); 7.20 (1H, dd, J=2, 9 Hz); 7.45 (1H, d, J=2 Hz).

Preparation (b)

5-[[(1,1-Dimethylethyl)amino]acetyl]-2-hydroxybenzaldehyde 4-methylbenzenesulfonate (6.18 g) is dissolved in anhydrous methanol (100 ml) and the solution cooled in an ice bath. To the cool, stirring solution is added sodium methoxide (0.93 g) and after 10 minutes 5% palladium on carbon (1.3 g) is added. The reaction mixture is hydrogenated at room temperature at 60 psi of hydrogen in a Parr apparatus. After 16 hours the reaction mixture is filtered thorough a pad of Celite ® and evaporated. Sodium 4-methylbenzene sulfonate is removed from the product by dissolving the crude material in methanol and triturating with ethylacetate as many times as necessary. In this way the title compound (3.1 g) is isolated as a homogeneous solid.

2. α¹-[[(1,1-DIMETHYLETHYL)AMINO]METHYL]-4-HYDROXY-1,3-BENZENEDIMETHANOL HEMISULFATE

α¹-[[(1,1-Dimethylethyl)amino]methyl]-4-hydroxy-1,3-benzenedimethanol (5.8 g) is dissolved in deionized water (8 ml) containing concentrated sulfuric acid (0.68 ml). The solution is stirred for 60 minutes, treated with ethanol (60 ml), stirred for 18 hours, treated with a further portion of ethanol (60 ml) and the title compound (3.35 g) isolated by filtration as a white powder.

NMR ((CD$_3$)$_2$SO): δ 1.25 (9H,s); 2.72–2.98 (2H, m); 4.49 (2H,s); 4.83 (1H, m); 6.75 (1H, d, J=10 Hz); 7.10 (1H, dd, J=2, 10 Hz); 7.32 (1H, d, J=2 Hz).

What is claimed is:

1. A compound of the formula

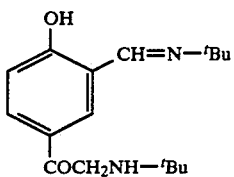

2. A method for the preparation of a compound of the formula

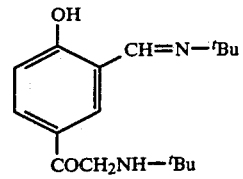

which comprises reacting a 5-(haloacetyl)-2-hydroxybenzaldehyde compound of the formula

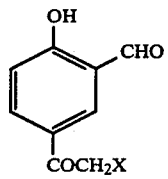

wherein X is bromo or chloro with 1,1-dimethylethanamine in an organic solvent in an inert atmosphere.

3. The method of claim 2 wherein the reaction is carried out in an inert atmosphere of nitrogen or argon.

4. The method of claim 2 wherein the reaction is carried out in an organic solvent selected from the group consisting of propan-2-ol, 1,1-dimethylethanol, 2-methyl-1-propanol and 2-butanol.

5. The method of claim 2 wherein the compound of formula III, X is bromo.

6. The method of claim 2 wherein the compound of formula III, X is chloro.

* * * * *